United States Patent [19]

Garrett et al.

[11] 4,342,696

[45] Aug. 3, 1982

[54] 7-DIMETHYLAMINO-3-SUBSTITUTED-2,2'-SPIROBI[2H-1-BENZOPYRANS]

[75] Inventors: Thomas B. Garrett, Lititz; John E. Herweh; Alan B. Magnusson, both of Lancaster, all of Pa.

[73] Assignee: Armstrong World Industries, Inc., Lancaster, Pa.

[21] Appl. No.: 277,176

[22] Filed: Jun. 25, 1981

Related U.S. Application Data

[63] Continuation-in-part of Ser. No. 195,320, Oct. 8, 1980, abandoned.

[51] Int. Cl.$^3$ .......................................... C07D 311/04
[52] U.S. Cl. ................................... 549/331; 430/345; 430/955
[58] Field of Search ...................................... 260/345.2

[56] References Cited

U.S. PATENT DOCUMENTS

| | | | |
|---|---|---|---|
| 2,978,462 | 4/1961 | Berman et al. | 260/345.2 |
| 3,022,318 | 2/1962 | Berman et al. | 260/345.2 |
| 3,666,525 | 5/1972 | Kimura et al. | 260/345.2 |
| 3,810,762 | 5/1974 | Laridon et al. | 260/345.2 |
| 3,810,763 | 5/1974 | Laridon et al. | 260/345.2 |
| 3,899,514 | 8/1975 | Baumann et al. | 260/345.2 |
| 3,971,808 | 7/1976 | Baumann et al. | 260/345.2 |
| 4,029,677 | 6/1977 | Baumann et al. | 260/345.2 |
| 4,110,348 | 8/1978 | Baumann et al. | 260/345.2 |

FOREIGN PATENT DOCUMENTS

10740  5/1980  European Pat. Off. ......... 260/345.2

OTHER PUBLICATIONS

Feichtmayr et al., Liebigs Ann. Chem., 1979 (9), 1337–45.

*Primary Examiner*—Nicky Chan

[57] ABSTRACT

Substituted spirobi[2H-1-benzopyrans] particularly suitable for use as precursors to stable colored pyrylium salts are disclosed.

2 Claims, No Drawings

7-DIMETHYLAMINO-3-SUBSTITUTED-2,2'-SPIROBI[2H-1-BENZOPYRANS]

This application is a continuation-in-part of U.S. Application Ser. No. 195,320 filed Oct. 8, 1980, now abandoned in the name of Thomas B. Garrett et al. and entitled "7-Dimethylamino-3-Substituted-2,2'-Spirobi[2H-1-Benzopyrans]."

This invention relates to spirobipyrans.

More specifically, this invention relates to spirobi[2H-1-benzopyrans].

Spirobipyrans are of interest as precursors for the UV generation of colored pyrylium salts for use in application as varied as optical data storage to the formation of non-contact decorative patterns (See. S. Maslowski, "High Density Data Storage UV Sensitive Tape," Applied Optics, 13, No. 4, 857 (1974).

The present invention provides a novel type of substituted spirobi [2H-1-benzopyran] particularly suitable for use as precursors to stable colored pyrylium salts.

According to this invention there is provided a compound having the formula wherein R represents $C_1$–$C_{12}$ alkyl, alkylene aryl, aryl or unsaturated alkyl.

The term "$C_1$–$C_{12}$ alkyl" is used in the specification and claims to signify a straight or branched alkyl group containing from 1 to 12 carbon atoms, with no more than 6 carbon atoms in its longest chain.

The term "aryl" is used in the specification and claims to signify phenyl or naphthyl, both of which may be unsubstituted or substituted in up to two positions with a substituent selected independently from $C_1$–$C_4$ alkyl, halo or —$NO_2$. "$C_1$–$C_4$ alkyl" is used above to signify a straight or branched alkyl group containing from 1 to 4 carbon atoms and "halo" is used above to signify fluoro, chloro, iodo and bromo.

The term "alkylene aryl" is used in the specification and claims to signify a moiety of the formula M—X—, wherein M represents aryl, as defined above, and X represents a straight or branched alkyl group having from 1 to 3 carbon atoms.

The term "unsaturated alkyl group" is used in the specification and claims to signify a straight or branched alkyl group containing at least 1 carbon - carbon double bond and having from 2 to 12 carbon atoms, with no more than 6 carbon atoms in its longest chain.

The novel substituted spirobi[2H-benzopyrans] of this invention are prepared via the straightforward reaction of a styryl ketone and 4-dimethylamino-2-hydroxybenzaldehyde according to the following reaction formula and as further illustrated in the Examples:

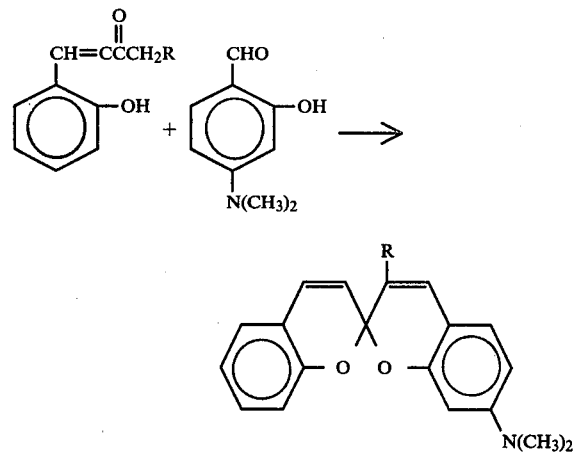

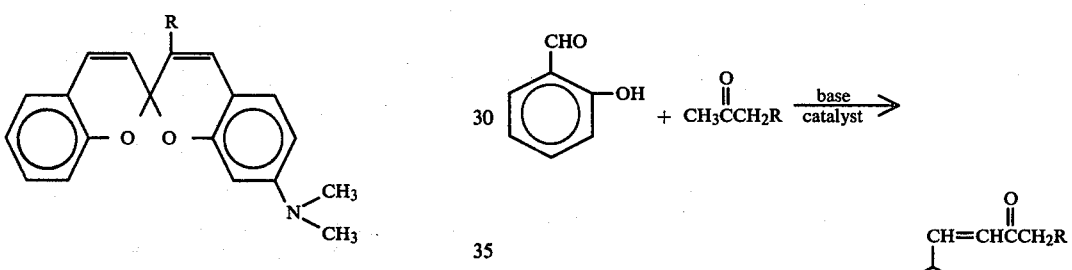

wherein R is defined above.

The styryl ketones specified above which are not available commercially can be prepared via the reaction of salicyl aldehyde and a corresponding ketone according to the following reaction formula:

The preparation of such styryl ketones is further documented in the literature: see *Organic Reactions*, vol. 16., J. Wiley and Sons, Inc., N.Y. 1968; E. D. Bergmann, A. Weizmann and E. Fischer, J. Am. Chem. Soc., 72 5009 (1950), D. M. Heilbron; F. Irving, J. Chem. Soc. 936 (1929) and A. McGookin and D. J. Sinclair. J. Chem. Soc., 127, 2539 (1925).

The stability of the colored pyrylium salts resulting from interaction of photogenerated protic acids with the spirobipyrans is important. It is known that the nature of ring substitution (see rings C and D, below) can influence stability. (G. Arnold, G. Paal, and H. P. Vollmer, Z. Naturforsch. B 25 (12), 1413 (1970); U.S. Pat. No. 3,733,197 to C. Schiele.)

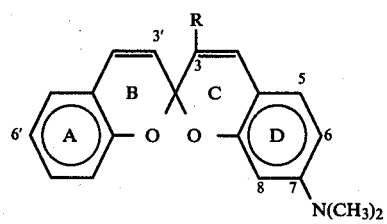

Further, it has now been found that substitution at the 7-position of ring D of a π electron donating group is effective in stabilizing the color of pyrylium salts. The compounds of this invention have been found to be particularly effective in this respect.

Reference is now made to the following examples which is provided to illustrate but not to limit the practice of this invention.

EXAMPLE I

This example demonstrates the preparation of 7-dimethylamino-3-methyl-2,2'-spirobi[2H-1-benzopyran].

To a solution of 2-hydroxystyryl ethyl ketone (1.76 g, 0.01 mol) and 4-dimethylamino-2-hydroxybenzaldehyde (1.65 g, 0.01 mol) in 25 ml of glacial acetic acid was added a cold solution of anhydrous hydrogen chloride (about 4 g) in 50 ml of glacial acetic acid. The steel blue solution rapidly turned deep magenta in color and was set aside.

After 16 hours at room temperature the dark colored mixture was cooled and filtered. The filter-cake was washed with ether, air-dried and gave about 2.0 gms of an iridescent green solid. This solid , believed to be the pyrylium salt, was suspended in acetone (75 ml), and the dark blue mixture carefully neutralized with dilute ammonium hydroxide (diluted concentrated ammonium hydroxide with water 1 to 1).

The pale yellow neutral reaction mixture containing a white solid (probably ammonium chloride) was filtered. The filtrate was concentrated to dryness under vacuum and left a deep blue residue. This residue was extracted with ether, and the combined ether extracts were dried over magnesium sulfate. The dried and filtered ethereal solution was concentrated to dryness and left a viscous dark blue oil. Repeated recrystallization of this colored residual oil from hot absolute alcohol gave pale green crystals (about 0.7 g), mp 148°–149°.

The resulting crystals were subjected to elemental analysis by Galbraith Laboratories Inc., Knoxville, TN and analysis was calculated for $C_{20}H_{19}NO_2$: C, 78.66; H, 6.27; N, 4.59. Found: C, 78.61; H, 6.49, N, 4.49.

The NMR spectral assignments for the resulting crystals are summarized below.

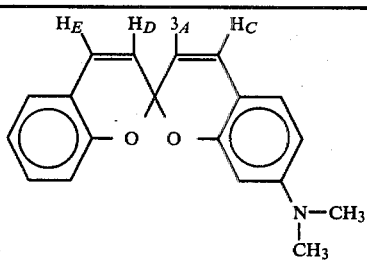

| Proton | $H_A$ | $H_B$ | $H_D$ | $H_C$ and $H_E$ | Aryl |
|---|---|---|---|---|---|
| Chemical* shifts, ppm | 1.93(s) | 2.8(s) | 5.92(d) | under aromatic protons | 6.1–7.3(c) |

*in $CDCl_3$ solvent, TMS as internal standard.

EXAMPLE 2

Preparation of 7-Dimethylamino-3-Allyl-2,2'-Spirobi[2H-1-benzopyran]—To a solution of 0.04 mol of 4-butyl-1-ene-ortho-hydroxy styryl ketone and 0.04 ml of 4-dimethylamino-2-hydroxybenzaldehyde in 50 ml of glacial acetic acid was added anhydrous hydrogen chloride with cooling. The anhydrous hydrogen chloride was added below the liquid surface. After ca. one hour, the hydrogen chloride addition was terminated and the deep magenta colored reaction mixture was stoppered and set aside. Following ca. 16 hours at room temperature, the reaction mixture was diluted with 200 ml of ether and viscous dark colored gum precipitated. The solvent layer was decanted, and the residual gum was triturated with fresh ether and then dried in vacuo.

The ether insoluble gum was slurried with 100 ml of acetone and the resulting mixture made weakly alkaline with dilute ammonium hydroxide while cooling in an ice bath. The deep red to amber colored reaction mixture (2 phases) was concentrated to near dryness on a rotary evaporator. The residue was extracted with ether and the combined ether washings dried over anhydrous magnesium sulfate.

After 16 hours the ethereal solution was filtered, concentrated to dryness on the rota-vap (<20 mm) and left a dark green viscous gum. Further drying in vacuo (<1 mm) converted this gum into a green solid. TLC on alumina (Alumina $60F_{254}$, E. Merck) developed with an ethyl acetate/hexane (50/50 by vol.) solvent mixture as the developing agent showed a single major product. Subsequently the crude product was chromatographed over Alumina and gave, after removal of solvent, 7.83 gms (59%) of a pale green solid, mp 63°–8°; UV max (THF) 225 nm (26,265), 312 (17,530); NMR ($CDCl_3$) 6.1–7.4 δ(m, 9, aryl and vinyl protons adjacent to aryl), 5.95 (d, 2, vinyl protons, ca. 5.9 (m. 1, methine associated with allyl group), 5.1 (m, 2, methylene of allyl group adjacent to ring), 2.97 (d, 2, terminal methylene of allyl group), 2.82 ppm (s, 6, methyl's of amino group). These values are consistent with the assigned structure:

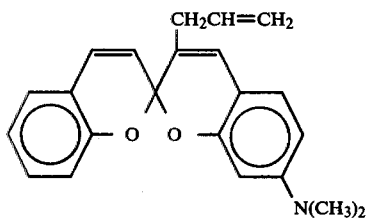

Analysis calcd. for $C_{22}H_{21}NO_2$: C, 79.72; H, 6.39; N, 4.23; Found: C, 79.03; H, 6.61; N.3.86

What is claimed is:

1. A compound having the formula

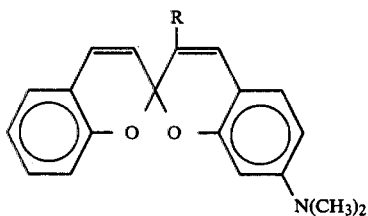

wherein R represents unsaturated alkyl.

2. The compound of claim 1 which is 7-dimethylamino-3-allyl-2,2'-spirobi[2H-benzopyran].